United States Patent [19]

Altenburger

[11] Patent Number: 5,185,146
[45] Date of Patent: Feb. 9, 1993

[54] RECOMBINANT MVA VACCINIA VIRUS

[75] Inventor: Werner Altenburger, Riehen, Switzerland

[73] Assignee: Hoffmann-LaRoche Inc., Nutley, N.J.

[21] Appl. No.: 293,738

[22] Filed: Jan. 4, 1989

[30] Foreign Application Priority Data

Jan. 12, 1988 [CH] Switzerland .............................. 85/88

[51] Int. Cl.$^5$ ...................... A61K 39/12; C12N 15/00
[52] U.S. Cl. ......................................... 424/89; 424/88; 435/69.1; 435/69.3; 435/172.1; 435/172.2; 435/172.3; 435/235.1; 435/236; 435/239; 435/240.1; 435/320.1; 935/12; 935/32; 935/57; 935/65
[58] Field of Search .............................. 424/89, 88, 93; 435/69.1, 69.3, 172.1, 172.2, 172.3, 235.1, 236, 237, 239, 240.1, 320.1; 935/12, 32, 57, 65

[56] References Cited

U.S. PATENT DOCUMENTS

| | | | |
|---|---|---|---|
| 4,603,112 | 7/1986 | Paoletti et al. | 435/235 |
| 4,722,848 | 2/1988 | Paoletti et al. | 424/89 |
| 4,769,330 | 9/1988 | Paoletti et al. | 435/172.3 |

FOREIGN PATENT DOCUMENTS

| | | |
|---|---|---|
| 083286 | of 0000 | European Pat. Off. . |
| 111385 | of 0000 | European Pat. Off. . |
| 198328 | of 0000 | European Pat. Off. . |
| 0261940 | 3/1988 | European Pat. Off. . |

OTHER PUBLICATIONS

Smith et al., Biotechnology & Genetic Engineering Reviews, Russell, Ed. vol. 2 383-407, Oct. 1984.

Primary Examiner—Johnnie R. Brown
Assistant Examiner—Abdel A. Mohamed
Attorney, Agent, or Firm—George M. Gould; William H. Epstein; John J. Schlager

[57] ABSTRACT

The present invention relates to recombinant vaccinia viruses which are derived from the modified virus Ankara (MVA) and which contain a DNA sequence which codes for a foreign antigen. The invention also relates to vaccines which contain a virus of this type in a form suitable for injection, as well as to a method for the preparation thereof. Furthermore, the invention relates to the use of a recombinant vaccinia virus MVA for the preparation of heterologous proteins in eukariotic cells.

5 Claims, No Drawings

RECOMBINANT MVA VACCINIA VIRUS

BACKGROUND OF THE INVENTION

Vaccinia viruses belong to the family of poxviruses. Certain strains of vaccinia viruses have been used for many years as live vaccine to immunize against smallpox, for example the Elstree strain of the Lister Institute in the UK. Because of the complications which may derive from the vaccination (compare Schär, Zeitschr. für Präventivmedizin 18, 41–44 [1973]), and since the declaration in 1980 by the WHO that smallpox had been eradicated nowadays only people at high risk are vaccinated against smallpox.

Vaccinia viruses have also been used recently as vectors for foreign antigens (Smith et al., Biotechnology and Genetic Engineering Reviews 2. 383-407 [1984]). This entails DNA sequences (genes) which code for foreign antigens being introduced, with the aid of DNA recombination techniques, into the genome of the vaccinia viruses. If the gene is integrated at a site in the viral DNA which is non-essential for the life cycle of the virus, it is possible for the newly produced recombinant vaccinia virus to be infectious, that is to say able to infect foreign cells and thus to express the integrated DNA sequence (compare European Patent Applications with the publication Nos. 83,286 [published on Jul. 6, 1983] and 110,385 [published on Jun. 13, 1984]). The recombinant vaccinia viruses prepared in this way can be used, on the one hand, as live vaccines for the prophylaxis of infections which are caused by these antigens or, on the other hand, for the preparation of heterologous proteins in eukaryotic cells. Most of the recombinant vaccinia viruses described in the literature are based on the WR strain. On the other hand, it is known that this strain has a high neurovirulence and is thus poorly suited for use in humans and animals (Morita et al., Vaccine 5, 65-70 [1987]).

However, strains of viruses specially cultured to avoid undesired side effects have been known for a long time. Thus, it has been possible, by serial passages of the Ankara strain of vaccinia virus (CVA) on chicken fibroblasts, to culture a modified vaccinia virus Ankara (MVA) (Swiss Patent No. 568,392). This modified vaccinia virus Ankara has only low virulence, that is to say it is followed by no side effects when used for vaccination. Hence it is particularly suitable for the initial vaccination of immunocompromised subjects. The excellent properties of the MVA strain have been demonstrated in a large number of clinical trials (Mayr et al., Zbl. Bakt. Hyg. I, Abt. Org. B 167. 375-390 [1978], Stickl et al., Dtsch. med. Wschr. 99, 2386-2392 [1974]).

Hence, a possible way to introduce foreign genes by DNA recombination into the MVA strain of vaccinia virus has been sought. Since the intention was not to alter the genome of the MVA except at the recombination site, it was necessary to use a method which complied with this requirement. Since the thymidine kinase gene (TK gene) of MVA is not of fundamental importance for the life cycle of the virus, the foreign DNA sequence was recombined in the DNA of the vaccinia TK gene.

SUMMARY OF THE INVENTION

The present invention relates to recombinant MVA vaccinia viruses which contain a gene which codes for a foreign antigen, preferably of a pathogenic agent, and to vaccines which contain a virus of this type in a physiologically acceptable form. The invention also relates to methods for the preparation of such recombinant MVA vaccinia viruses or vaccines, and to the use of these vaccines for the prophylaxis of infections caused by such antigens or pathogenic agents.

The recombinant MVA vaccinia viruses can be used to prepare heterologous polypeptides in eukaryotic cells. This entails cells being infected with the recombinant vaccinia viruses. The gene which codes for the foreign antigen is expressed in the cells. The expressed heterologous polypeptide can be isolated. The methods to be used for the production of such heterologous polypeptides are generally known to those skilled in the art (compare, for example, European Patent Applications with the publication numbers 206,920 [published on Dec. 30, 1986] and 205,939 [published on Dec. 30, 1986]. The polypeptides produced with the aid of the recombinant MVA viruses are, by reason of the special properties of the MVA viruses, more suitable for use as medicaments in humans and animals.

The recombinant MVA vaccinia viruses can be prepared as set out hereinafter. Eukaryotic cells, preferably mammalian cells, especially CV1 monkey cells (obtainable from Flow Laboratories, Catalogue No. 02-240, from the American Type Culture Collection (ATCC), 12301 Parklawn Drive, Rockville, Md., U.S.A., under Depositary No. CCL 70, and from the European Collection of Animal Cell Cultures (ECACC), PHLS Centre for Applied Microbiology and Research, Porton Down, Salisbury, Great Britain, under Depositary No. 85011434; described by Jensen et al., Proc. Natl. Acad. Sci. USA 52, 53-59 [1964]) can be infected with the MVA. MVA and its properties are described in detail in the literature (Mayr et al., supra). The MVA virus was deposited in compliance with the requirements of the Budapest Treaty at CNCM (Institut Pasteur, Collection Nationale de Cultures de Microorganisms, 25, rue du Docteur Roux, 75724 Paris Cedex 15) on Dec. 15, 1987 under Depositary No. I-721. The MVA virus can be grown on chicken embryo fibroblasts (CEF) as described in the example. MVA is distinguished by its great attenuation, that is to say by diminished virulence or infectiosity while maintaining good immunogenicity. The extent of diminution of the virulence can be determined experimentally in a variety of ways, for example by the behaviour of the virus on cell cultures, by measurement of the neurovirulence; or of the virulence on subcutaneous administration, or by a virulence assay in immunosuppressed mice. The highly attenuated MVA strain shows a great change in the behaviour on cell cultures and a neurovirulence which is at least a factor of $10^7$ less than that of the wild-type WR of vaccinia virus. This difference is also evident on comparison of recombinant wild-type viruses of the WR strain with recombinant viruses of the MVA strain.

DESCRIPTION OF THE INVENTION

According to the present invention, a DNA which contains a partial sequence from a non-essential segment of the vaccinia virus, DNA, and a DNA sequence which codes for a foreign antigen, is introduced into the infected cell.

The DNA can be introduced into the cells by transfection, for example by means of calcium phosphate precipitation (Graham et al., Virol. 52, 456–467 [1973]; Wigler et al., Cell 777-785 [1979], by means of electroporation (Neumann et al., EMBO J. 1, 841-845

[1982]), by microinjection (Graessmann et al., Meth. Enzymology 101, 482-492 [1983]), by means of liposomes (Straubinger et al., Methods in Enzymology 101, 512-527 [1983]), by means of spheroplasts (Schaffner, Proc. Natl. Acad. Sci. USA 77, 2163-2167 [1980]) or by other methods known to those skilled in the art. Transfection by means of calcium phosphate precipitation is preferably used.

The inserted DNA can be linear or circular. A circular DNA is preferably used. It is particularly preferable to use a plasmid. The DNA contains at least one partial sequence from a non-essential segment of the vaccinia virus DNA. Non-essential segments of the vaccinia virus DNA are known to those skilled in the art. One example of a non-essential segment of this type is the thymidine kinas gene and its adjacent regions (Weir et al., J. Virol., 530-537 [1983]). The preferred partial sequence is contained in the plasmid pHGS-2/5.1, whose construction is described in the European Patent Application with the publication No. 198,328, published on Oct. 22, 1986.

The plasmid pHGS-2/5.1 contains a gene which codes for the 5.1 antigen of the malaria pathogen Plasmodium falciparum (Hope et al., Nucleic Acids Res. 13, 369-379 [1985]). The DNA can contain, in place of this gene which codes for a malaria antigen, other known genes from pathogenic agents. Pathogenic agents are to be understood to be viruses, bacteria and parasites which may cause a disease, as well as tumor cells which multiply unrestrictedly in an organism and may thus lead to pathological growths. Examples of such pathogenic agents are described in Davis, B.D. et al., (Microbiology, 3rd ed., Harper International Edition). Preferred genes of pathogenic agents are those of the malaria parasite Plasmodium falciparum, of the tuberculosis-causing Mycobacteria, of herpes viruses and of human immunodeficiency viruses, for example HIV I and HIV II.

In order for it to be possible for the DNA sequence or the gene which codes for a foreign antigen to be expressed, it is necessary for regulatory sequences, which are required for the transcription of the gene, to be present on the DNA. Such regulatory sequences (called promoters) are known to those skilled in the art, for example those of the vaccinia 11 kDa gene as are described in European Patent Application, Publication No. 198,328, and those of the 7.5 kDa gene (European Patent Application, Publication No. 110,385).

Once the gene coding for a foreign antigen has been introduced into the eukaryotic cell and the foreign DNA has recombined with the viral DNA, it is possible to isolate the desired recombinant vaccinia virus in a manner known per se, preferably with the aid of a marker (compare Nakano et al., Proc. Natl. Acad. Sci. USA 79, 1593-1596 [1982], Franke et al., Mol. Cell. Biol. 1918-1924 [1985], Chakrabarti et al., Mol. Cell. Biol. 3403-3409 [1985], Fathi et al., Virology 97-105 [1986]). This is preferably carried out, as described in the examples, by adding the infected eukaryotic cells, two days after transfection, to 143B TK− cells (ATCC No. CRL 8303) and incubating the latter in the presence of bromodeoxyuridine (BUdR) for a further two days. During this, all the cells which contain a functional thymidine kinase gene (TK gene) are killed, and only the TK− cells, as well as TK− cells which contain a vaccinia virus genome in which the TK gene has been inactivated by integration of a foreign gene, are now able to survive.

This selection step is preferably carried out several times. In order to obtain single viral clones, it is possible after the BUdR selection to infect primary chicken embryo fibroblasts (CEF) with the cell suspension of 143B TK− cells and to incubate them under an agarose medium as described in the example. The expression of the foreign antigen can be detected in the cloned viruses by means of fluorescent antibodies. Positive clones can be further purified by plaque purification. The recombinant MVA vaccinia viruses obtained in this way are able to express the gene which codes for a foreign antigen and is contained in the viral genome. It has emerged that the expression of such genes is approximately equally strong in recombinants of the greatly attenuated MVA strain and in recombinants of the WR strain customarily used.

To prepare vaccines, the MVA vaccinia viruses according to the invention are converted into a physiologically acceptable form. This can be done based on the many years of experience in the preparation of vaccines used for vaccination against smallpox (Kaplan, Br. Med. Bull. 25, 131-135 [1969]). Typically, about $10^6$-$10^7$ particles of the recombinant MVA are freeze-dried in 100 $\mu$l of phosphate-buffered saline (PBS) in the presence of 2% peptone and 1% human albumin in an ampoule, preferably a glass ampoule. The lyophilisate can contain extenders (such as mannitol, dextran, sugar, glycine, lactose or polyvinylpyrrolidone) or other aids (such as antioxidants, stabilizers, etc.) suitable for parenteral administration. The glass ampoule is then sealed and can be stored, preferably at temperatures below $-20°$ C., for several months.

For vaccination the lyophilisate can be dissolved in 0.1 to 0.2 ml of aqueous solution, preferably physiological saline, and administered parenterally, for example by intradermal inoculation. The vaccine according to the invention is preferably injected intracutaneously. Slight swelling and redness, sometimes also itching, may be found at the injection site (Stickl et al., supra). The mode of administration, the dose and the number of administrations o can be optimized by those skilled in the art in a known manner. It is expedient where appropriate to administer the vaccine several times over a lengthy period in order to obtain a high titre of antibodies against the foreign antigen.

The detailed example which follows is intended to contribute to a better understanding of the present invention. However, it is not intended to give the impression that the invention is confined to the subject-matter of the example.

EXAMPLE

1. Growing and purification of the viruses 1.1 Growing of the MVA virus

The MVA virus is a greatly attenuated vaccinia virus produced by serial passages of the original CVA strain on chicken embryo fibroblast (CEF) cultures. For a general review of the history of the production, the properties and the use of the MVA strain of vaccinia, reference may be made to the summary published by Mayr et al. in Infection 3, 6-14 [1975]. Owing to the adaptation to CEF, growth of the MVA virus on other cell systems is greatly restricted, and plaque formation by the virus is now detectable only on CEF cells. Although no plaque formation can be found on monkey CVl (ATCC No. CCL 70) and human 143B TK− cells (ATCC No. CRL 8303; Bacchetti et al., Proc. Natl.

Acad. Sci. USA 74, 1590-1594 [1977]), it was nevertheless possible to show, as described hereinafter, that replication of the MVA virus takes place at least on these two cell lines and is approximately comparable to that on CEF cells. The ability of the MVA virus to replicate on CV1 and 143B TK− cells was utilized for the recombination of foreign antigens into the viral genome (see below). However, in order not to alter the properties of the MVA virus it was normally grown on CEF cells, the host cell for which it had been adapted. To prepare the CEF cells, 11-day old embryos were isolated from incubated chicken eggs, the extremities were removed, and the embryos were cut into small pieces and slowly dissociated in a solution composed of 0.25% trypsin at room temperature for 2 hours. The resulting cell suspension was diluted with one volume of medium I (MEM Eagle, for example obtainable from Gibco, Basle, Switzerland; Order No. 072-1500) containing 5% fetal calf serum (FCS), penicillin (100 units/ml), streptomycin(100 μg/ml)and 2 mM glutamine and filtered through a cell screen (for example obtainable from Technomara AG, Zurich, Switzerland, Order No. Bellco 1985, 150 mesh), and the cells were sedimented by centrifugation at 2000 rpm in a bench centrifuge (Hermle KG, D-7209 Gosheim, FRG) at room temperature for 5 minutes. The cell sediment was taken up in ¼ of the original volume of medium I, and the CEF cells obtained in this way were spread on cell culture dishes. They were left to grow in medium I in a $CO_2$ incubator at 37° C. for 1-2 days, depending on the desired cell density, and were used for infection either directly of after 1-2 further cell passages. A clear description of the preparation of primary cultures can be found in the book by R. I. Freshney, "Culture of animal cells", Alan R. Liss Verlag, New York [1983], Chapter 11, page 99 et seq.

MVA viruses were used for infection as follows. CEF cells were cultured in 175 $cm^2$ cell culture bottles. At 80-90% confluence, the medium was removed and the cells were incubated for one hour with an MVA virus suspension (0.01 infectious particles (=pfu) per cell, 0.01 ml/$cm^2$) in phosphate-buffered saline (PBS/Dulbecco, for example Animed AG, Muttenz, Switzerland, Order No. 23.100.10). Then medium I was added (0.2 ml/$cm^2$) and the bottles were incubated at 37° C. for 2-3 days until about 80% of the CEF cells had lysed. The virus lysates were stored with the cells and medium, without treatment, in the cell culture bottles at −30° C. before further processing (purification etc.).

1.2 Growing of the WR virus.

In contrast to the MVA virus, the WR virus (ATCC No. VR-119) is able to grow in virtually all cell lines (Drillien et al., J. Virology 843-850 [1978]) and its growth can be observed directly by means of plaque formation. Thus, although there was no pressing reason to grow this virus on CEF cells, nevertheless these cells were usually chosen in the experiments described hereinafter, in order to eliminate as far as possible factors specific to the host cells in the direct comparison of the two viruses, MVA and WR. Growing was carried out as described for the MVA virus.

1.3 Purification of the viruses

The purification steps undertaken to obtain a virus preparation which was as pure as possible and free from components specific to the host cell were identical for the MVA and WR viruses (Joklik, Virology 18, 9-18 [1962], Zwartouw et al., J. gen. Microbiol 29, 523-529 [1962]). The cell cultures which had been infected and then stored at −30° C. were thawed, the residual cells were shaken off or scraped off the plastic substrate, and cells and virus were removed from the medium by centrifugation (Sorvall centrifuge, GSA rotor, 1 hour at 5000 rpm and 10° C.). The sediment, composed of viral and cell particles, was suspended once in PBS (10-20 times the volume of the sediment), and the suspension was centrifuged as above. The new sediment was suspended in 10 times the volume of RSB buffer (10 mM Tris-HCl pH 8.0, 10 mM KCl, 1 mM $MgCl_2$), and the suspension was briefly treated with ultrasound (Labsonic 1510 equipped with a 4 mm diameter tip, obtainable from Bender and Hobein, Zürich, Switzerland; 2×10 seconds at 60 watts and room temperature) in order to disintegrate remaining still intact cells and to liberate the virus particles from the cell membranes. The cell nuclei and the larger cell debris were removed in the subsequent brief centrifugation of the suspension (Sorvall GSA rotor obtainable from DuPont Co., D-6353 Bad Nauheim, FRG; 3 minutes at 3000 rpm and 10° C.). The sediment was once again suspended in RSB buffer, treated with ultrasound and centrifuged, as described above. The collected supernatants containing the free virus particles were combined and layered over a pad composed of 10 ml of 35% sucrose in 10 mM Tris-HCl, pH 8.0, and centrifuged in a Kontron TST 28.38/17 rotor (Kontron Instrumente, Zürich, Switzerland; corresponds to a Beckman SW 27 rotor) for 90 minutes with 14,000 rpm at 10° C.). The supernatant was decanted, and the sediment containing the virus particles was taken up in 10 ml of 10 mM Tris-HCl, pH 8.0, homogenized by brief treatment with ultrasound (2×10 seconds at room temperature, apparatus as described above), and applied to a stepped gradient for further purification. The steps of the gradient were each composed of 5 ml of sucrose in 10 mM Tris-HCl, pH 8.0 (sucrose concentration steps: 20%, 25%, 30%, 35% and 40%). The gradient was centrifuged in a Kontron TST 28.38/17 rotor at 14,000 rpm 10° C. for 35 minutes. After this centrifugation, several discrete zones containing virus particles were visible in the region of the gradient between 30% and 40% sucrose. This region was siphoned off from the gradient (10 ml), the sucrose solution was diluted with PBS (20 ml) and the virus particles were sedimented therefrom by centrifugation (Kontron TST 28.38/17 rotor, 90 minutes at 14,000 rpm, 10° C.). The sediment, which now consisted mostly of pure virus particles (comparison between OD measurement and plaque test, see below), was taken up in PBS in such a way that the virus concentrations corresponded on average to 1-5×$10^9$ pfu/ml. The purified virus stock solution was used either directly or diluted with PBS for the subsequent experiments.

1.4 Determination of concentration

The determination of the concentration of the virus preparations was usually carried out in two ways and thus also permitted a statement to be made about the purity of the virus stock. The absolute concentration of virus particles in the solution was determined by measurement of the optical density of the virus solution at 260 nm in a spectrophotometer where 1 $OD_{260}$ corresponds to a virus concentration of 1.2×$10^{10}$ particles per ml (Joklik, supra). For this purpose, the above virus solutions were diluted in the ratio 1:100 with PBS, and the absorption was measured in quartz cuvettes with PBS solution as reference. Assuming that only about every sixtieth virus particle from a preparation of this type is able to infect cell culture cells, that is to say is infectious (Joklik, Bacteriol. Rev. 30, 33–66 [1966]), it is possible to compare directly the virus titre calculated from the measurement of optical density and the virus titre obtained by the method described hereinafter.

For titrating out the virus solutions on cell cultures, CEF cultures were grown in medium I in 8 cm² plastic cell culture dishes. The medium was aspirated from dishes which were 80–90% confluent, and 0.2 ml of virus diluted with PBS was added to each. The dishes were then left to stand at room temperature for 1 hour. The virus solution was diluted in decimal steps. After this incubation at room temperature, 2 ml of agarose medium I (consisting of medium I+1% agarose) were added to each dish, and the dishes were incubated in a $CO_2$ incubator for 16–24 hours. Then a layer Of 2 ml of agarose medium I, which contained in addition 0.2% neutral red for staining the live cells, was Placed on top, and the dishes were incubated for a further 16–24 hours. After this time had elapsed, it was possible to count the colourless plaques under a binocular, and the resulting number of plaques was compared with the value calculated from the optical density. Good agreement was found in most cases. The virus titre calculated from the optical measurement was usually a factor of about 2 to 4 higher.

1.5 Growing of the MVA virus in various cell lines (+++++) in most cases. See left-hand side of Table I.

It is not possible to establish from the experiment described above whether growth of the MVA virus has taken Place in the various cell lines or not. For this reason, the medium and the cells from each of the remaining, unstained culture dishes were collected, briefly homogenized with ultrasound, and in homogenates obtained in this way were used to infect CEF cells. The homogenates were diluted with PBS in the ratio 1:20, 1:100 and 1:500. 0.2 ml of each of the dilutions was added to 2 dishes of CEF cells which were 80–90% confluent and from which the medium had previously been removed. The cells were incubated at room temperature for one hour and then a layer of agarose medium I was placed on top (2 ml/dish). After incubation at 37° C. for 16–24 hours, agarose medium I containing 0.2% neutral red was added (2 ml/dish) and the dishes were incubated for a further 16–24 hours. The colourless plaques were now readily visible and were counted (pfu/dish). The results for the individual cell lines are recorded in the right hand side of Table I. These are the figures for the dilutions of the intermediate virus concentrations (1 pfu/50 cells). From the original number of MVA virus particles used (pfu/cell), the dilution of the homogenates and the volume used for infection of the CEF cells it is possible to calculate the number of virus particles which were placed on the CEF (=amount of virus added), assuming that the MVA virus had not grown in the individual cell lines. It is evident from the table that the number of plaques was

TABLE I

|  | 1/500 | 1/50 | 1/5 | 1:20 | 1:100 | 1:500 |
|---|---|---|---|---|---|---|
| LM TK⁻ | ++ | ++ | +++ | 5/9 | 0/0 | 0/0 |
| RK13 | + | + | ++++ | 10/13 | 3/3 | 1/0 |
| CV1 | ++ | +++ | ++++++ | nd | 500/nd | 110/140 |
| RITA | ++ | +++++ | ++++++ | 31/38 | 10/5 | 3/0 |
| HeLa | ++ | ++ | ++++++ | 31/39 | 10/9 | 1/0 |
| AG1523 | +++++ | +++++ | ++++++ | 11/8 | 1/0 | 0/0 |
| 143B TK⁻ | ++ | +++++ | ++++++ | 156/nd | 60/86 | 30/29 |
|  |  |  |  | 25 | 5 | 1 |
|  |  |  |  | Amount of virus added | | |

(nd = not determined)

The cell lines LM TK⁻ (ATCC No. CCL 1.3), RK13 (ATCC No. CCL 37), CV1 (ATCC No. CCL 70), Rita (RC-37, Schröder et al., J. gen. Virol. 41, 493–501 [1978]), HeLa (ATCC No. CCL 2), AG1523 (Human Genetic Mutant Cell Repository, National Institute of General Medical Science NIGMS, Camden, N.J., USA) and 143B TK⁻ (ATCC No. CRL 8303) listed in Table I were spread out in 8 cm² dishes (12 dishes for each line) and left to grow under medium I to 80–90% confluence in a $CO_2$ incubator at 37° C. The medium was then aspirated off, and the cells were each infected wit 0.2 ml of MVA virus (in PBS), specifically in concentrations of one infectious virus particle (pfu) per 500, 50 or 5 cells, respectively. After 1 hour at room temperature, 2 ml of medium I were added to the cells and the latter were incubated at 37° C. After 2 days, medium was removed from one half of the culture dishes, and the cells were fixed and stained with a solution of 2% neutral red in 18% ethanol (1 ml/dish). No plaques were detectable in any of the stained cultures, but the cells in each culture showed cytopathic effects (cell changes) which could be pronounced (++++) or weak (+) depending on the cell line. High virus concentrations (1 pfu/5 cells) resulted in general cell death significantly above the figure expected from the amount of virus added only in two of the tested cell lines (CV1 and 143B TK⁻), that is to say measurable growth of the MVA virus had taken place only in these two cell lines.

2. Insertion of a foreign antigen 2.1 Plasmid with the malaria 5.1 antigen

The foreign antigen was inserted into the vaccinia virus genome by the method described by Mackett et al., (Proc. Natl. Acad. Sci. USA 79, 7415–7419 [1982]) which is based on homologous recombinations in the viral TK gene. The construction of the plasmid pHGS-2/5.1 which was used for the recombination in the present example is described in detail in European Patent Application, Publication No. 198,328, published on Oct. 22, 1986. The starting plasmid pHGS-2 was deposited, in the form of a culture of E. coli HB101 transformed with the plasmid pHGS-2, in compliance with the Budapest Treaty, on Feb. 21, 1985 under Depositary No. DSM 3249 at the Deutsche Sammlung von Mikroorganismen DSM in Gottingen, Germany, and was made freely available on Oct. 4, 1986. The DSM is located in D-3300 Braunschweig at Mascheroder Weg IB since November 1987.

2.2 Recombination of the WR virus

The recombination of the 5.1 antigen in the WR virus was carried out by a protocol which permits double selection for recombinant viruses. In a first step, medium was removed from 8 cm² culture dishes containing CV1 monkey cells which were 80–90% confluent, and then a layer of 0.2 ml of a virus suspension of the temperature-sensitive vaccinia mutant ts N7 (Drillien et al., Virology 131, 385–393 [1983]) was placed on top (0.1 pfu/cell). The dishes were left to stand at room temperature for 1 hour. Then medium I was added (2 ml/dish) to the infected cells, and the dishes were incubated in a $CO_2$ incubator at the temperature of 33° C. which is permissive for the virus, for 2 hours (Kieny et al., Nature 312, 163–166 [1984]). Half an hour before this incubation time had elapsed, a calcium phosphate precipitate containing the DNAs was prepared (Graham et al., supra). For this purpose, 0.55 ml of HeBS buffer (1.5 mM disodium hydrogenphosphate, 280 mM NaCl, 50 mM HEPES adjusted to pH 7.1) was introduced, followed by 200 ng of purified vaccinia WR virus DNA and 200 ng of the purified plasmid pHGS-2/5.1 DNA, each in 1 µl of TE buffer (10 mM Tris-HCl pH 7.5, 1 mM EDTA). 0.55 ml of a 250 mM calcium chloride solution was added dropwise, while agitating gently, and the mixture was left to stand at room temperature for 20 minutes. The medium was then drawn off from the culture dishes, and the cells were mixed in each case with 0.25 ml of the precipitate containing the DNAs. After incubation at room temperature for one hour, 2 ml of medium I were added to each, and the cells were incubated in a $CO_2$ incubator at 39.5° C. for 2 hours (Kieny et al., supra). The ts N7 viruses originally used are unable to grow at this raised temperature, which permits selection of viruses which have undergone recombinations in the ts7 locus at least. Since the calcium phosphate lying on the cells had, in the long term, adverse effects on cell growth, the medium was removed after incubation for two hours, the cells were washed 3 times with 1 ml of PBS each time, agitating gently, the PBS solution was aspirated off each time, 2 ml of medium I was again added to the cells in each case, and the latter were kept in a $CO_2$ incubator at 39.5° C. for a further 2 days. The culture dishes containing the cells and the medium were then frozen at −30° C., thawed again, the still adhering cells were scraped off the dishes, and the suspension was treated briefly with ultrasound as described above. For the second selection step, 0.2 ml of this homogenate, undiluted or diluted 1:5 or 1:30, respectively, with PBS, was placed in each case on an almost confluent lawn of human 143B TK⁻ cells in 8 cm² culture dishes from which the medium had previously been removed. The infected cells were maintained at room temperature for 1 hour and then a layer of 2 ml of agarose medium II (medium I plus non-essential amino acid solution [Gibco; Order No. 043-1140] plus vitamins [Gibco; Order No. 043-1120] plus 1% agarose) containing 0.1 mg/ml bromodeoxyuridine (BUdR) was placed on each. The dishes were then incubated in a $CO_2$ incubator at 37° C. for 16–24 hours. A second layer of agarose medium II, but containing in addition 0.2% neutral red, was placed on top, and the dishes were incubated for a further 16–24 hours. After this time the colourless plaques were normally readily visible, and it was possible to remove the virus contained therein in form of an agarose cylinder, as a single clone by stabbing with a Pasteur pipette (plaque purification). Clones removed by stabbing in this way were grown on CV1 cells as usual and, after growing, subjected to a second and third plaque purification. The final growing and purification of the recombinant WR 5.1 virus obtained in this way were carried out as described above.

2.3 Recombination in the MVA virus

As discussed above, and as set out in Table I, the MVA virus is, although no plaque formation occurs, able to grow in CV1 and 143B TK⁻ cells. This fact facilitates recombination of foreign antigens in the TK gene of the MVA virus in two ways. On the one hand, it has emerged from the experiments that CV1 cells provide a better host than CEF for the recombination process. On the other hand, owing to the replication of the virus in 143B TK⁻ cells, selection for TK⁻ virus is also simplified.

The recombination of foreign antigens in the MVA virus differs, essentially in two respects, from the method described for the WR virus. On the one hand, it was not possible, in order not to alter the structure of the MVA virus except in the TK gene, to use selection via the temperature-sensitive virus ts N7. On the other hand, in the BUdR selection the 143B TK⁻ cells were mixed not with agarose medium II but with normal medium II (medium I plus non-essential amino acid solution [Gibco, Order No. 043-1 140] plus vitamins [Gibco; Order No. 043-1120], and the removal of individual plaques by stabbing was not carried out until after infection of CEF with the selected TK⁻ virus and incubation under agarose medium I.

The recombination protocol used for the MVA virus approximately corresponds to the method described by Mackett et al., (Proc. Natl. Acad. Sci. USA 79, 7415–7419 [1982]) for the WR virus. Medium was removed from CV1 cells on 8 cm² culture dishes at 80–90% confluence, a layer of 0.2 ml of an MVA virus suspension was placed on top of each (0.1 pfu/cell) and they were incubated at room temperature for 1 hour. Then 2 ml of medium I were pipetted to each of the infected cells, and the cells were incubated in a $CO_2$ incubator at 37° C. for 2 hours. The following steps correspond to the method used for the WR virus (see above), except that no WR virus DNA was added for making the calcium phosphate precipitation, the subsequent incubation of the cells was carried out at 37° C., and a layer of 2 ml of medium II without agarose but with 0.1 mg/ml BUdR was placed on top of the 143B TK⁻ cells. After incubation for 2 days, the culture dishes were briefly cooled to −30° C., the solution was thawed again, the remaining cells were scraped off the substrate, and cells and medium were homogenized by brief ultrasound treatment as described above. After removal of the medium from 8 cm² culture dishes which were 80–90% overgrown with CEF, various dilutions of this homogenate were added to the cells (0.2 ml/dish) and the infection was maintained at room temperature for 1 hour. Then a layer of 2 ml of agarose medium I was placed on top of the CEF, which were incubated at 37° C. for 16–24 hours, and then a second layer of agarose medium I (2 ml) which additionally contained 0.2% neutral red was placed on top. After a further 16–24 hours, the colourless plaques were readily visible, and it was possible to remove the virus contained therein, together with the overlying agarose, by stabbing with a Pasteur pipette. The virus clone isolated in this way was grown on CV1 cells and, to purify the virus clone, selection on 143B TK⁻ cells and the subsequent steps were repeated 1-2 times (plaque purification). The final growing and purification of the recombinant MVA 5.1 virus obtained in this way were carried out in the manner described above.

3 Expression of the 5.1 antigen 3.1 In vitro expression in cell cultures

In order to test the expression of the malaria 5.1 Ag by the recombinant WR 5.1 and MVA 5.1 viruses in CV1 cells, CV1 cells infected with recombinant virus were sedimented by brief centrifugation in a bench centrifuge (Hettich Mikrorapid K, obtainable from A. Hettich AG, Bäch, Switzerland; max. speed for 3 minutes at 20° C.), and the sediment was washed twice with PBS, taken up in PBS and applied to a glass microscope slide and left to dry there. Another method comprised culturing CV1 cells directly on a slide, infecting them with the virus, after 1-2 days removing incubation medium from the cells infected in this way by washing with PBS, and allowing them to dry on the glass slide at room temperature. To fix the cells, the slides were incubated in acetone at −30° C. for at least 1 hour and then left to dry at room temperature.

Rabbit anti-5.1 antiserum diluted in PBS was placed on the prepared slides in such a way that the cells were covered with a layer of liquid. The slides were incubated in a humidity chamber at 37° C. for 1 hour, then washed several times with PBS and, without allowing them to dry, the second antibody, labelled with fluorescein isothiocyanate (FITC) and diluted in PBS (goat anti-rabbit IgG, Nordic GAR/Ig/FITC, obtainable from Biogenzia Lemania SA, Lausanne, Switzerland), was added to the cells. After incubation in a humidity chamber at 37° C. for one hour, the slides were washed several times with PBS and left to dry thoroughly. It was then possible to test the cell preparations for fluorescence emission in a microscope under UV light.

3.2 In vivo expression in mice

In order to be able to compare the expression of the malaria 5.1 antigen by the recombinant MVA virus with that of the recombinant WR virus in vivo, the anti-5.1 antibody production in mice which had been immunized with either of these recombinant viruses was measured. For this purpose, Swiss albino mice were injected subcutaneously twice, at an interval of 2 weeks, either with the 5.1 recombinant of the WR virus ($10^8$ pfu/mouse) or the 5.1 recombinant of the greatly attenuated MVA virus ($10^9$ pfu/mouse). 2 weeks after the final injection, the tip of the tail was cut off and a little blood was aspirated into a heparinized capillary (10 μl mouse). The capillary was blown out into 90 μl of PBS, and the serum fraction was obtained from this solution by centrifugation. Various serial dilutions of the serum were tested in an ELISA (Voller et al., The enzyme-linked immunosorbent assay (ELISA), Dynatech [1979], obtainable from Dynatech Produkte AG, Embrach, Switzerland) for the amount of antibodies contained therein and directed against the malaria 5.1 antigen. For this purpose, multititre plates (for example Dynatech Produkte AG; Order No. 655001) were coated with 0.25 μg/well of recombinant 5.1 antigen isolated from E. coli (Hope et al., Nature 308, 191-194 [1984]). The results of a comparative experiment of this type are compiled in Table II.

TABLE II

| | | Antibody production anti-5.1 antigen ELISA titre | |
|---|---|---|---|
| a) | WR 5.1 | ($10^8$ pfu/mouse) | |
| | | 1:15,000 | |
| | | 1:31,000 | |
| | | 1:30,000 | 1:22,800 |
| | | 1:30,000 | |
| | | 1:8,000 | |
| | WR WT | | 1:200 |
| b) | MVA 5.1 | ($10^9$ pfu/mouse) | |
| | | 1:6,000 | |
| | | 1:6,500 | |
| | | 1:8,000 | 1:6,700 |
| | | 1:7,100 | |
| | | 1:6,000 | |
| | MVA WT | | 1:250 |

Groups of five 3-week old Swiss Albino mice were immunized as described above a) with the recombinant WR vaccinia virus (WR 5.1) or b) with the recombinant MVA vaccinia virus (MVA 5.1), and the titres of anti-5.1 antibody in the serum were determined by ELISA. In addition, as a control inoculation, groups of 2 mice were injected with the corresponding amount of the starting viruses (WR WT or MVA WT). Whereas the titres measured in the control sera were 1:200 (WR WT) and 1:250 (MVA WT), the values in the sera from the animals treated with the recombinant viruses were an average of a factor of 30 (MVA 5.1) or 120 (WR 5.1) above the value for the control sera.

4. Virulence behaviour of the recombinant MVA virus 4.1 Behaviour in cell cultures.

In contrast to the starting virus (MVA WT) the recombinant MVA virus (MVA 5.1) forms plaques on CV1 cells. Hence, it gave the impression that the behaviour of the recombinant MVA virus in cell cultures had altered slightly compared with the MVA starting virus. Since this alteration was not attributable to a contamination by other strains of virus, the suspicion arose that the virulence might have increased or the host-virus behaviour might have changed due to the recombination of the 5.1 antigen in the viral TK gene.

4.2 Neurovirulence in mice

The slight alteration in the behaviour of the recombinant MVA virus in cell cultures, namely the formation of plaques on CV1 cells, prompted the question of whether there had possibly been an increase in the virulence caused by the insertion of the foreign DNA into the viral thymidine kinase gene. One possible way of examining this question was to measure the neurovirulence of the viruses. For this purpose, the $LD_{50}$ value was determined after intracerebral injection of the viruses into 1- to 2-day old mice. Firstly, the concentrations of all five tested viruses were adjusted to an initial concentration of $4\times10^9$ pfu/ml with PBS. Starting from these, 10-fold dilutions in PBS were prepared, down to a concentration of $4\times10^2$ pfu/ml. The viruses used were the WR virus (ATCC No. VR-119=WR WT), the recombinant WR 5.1 virus based thereon (WR 5.1), the Elstree virus (ATCC No. VR-862 LS WT), the MVA starting virus (MVA WT), and its 5.1 recombinant (MVA 5.1). 1- to 2-day old mice (Swiss albino) were divided into groups of 5 mice and, in each case, 2 such groups were left in the care of a mother mouse in a cage. 5 mice for each type of virus and virus concentration received injections of 10 μl of the virus suspension into the left half of the brain, and the behaviour of the animals was observed for a period of two weeks, or until they died. The $LD_{50}$ value for a type of virus was calculated from the survival rate of the mice in the individual groups using the formula of Reed et al. (Amer. J. Hyg. 27, 493-497 [1938]). The results of these experiments are compiled in Table III. It emerges that no increase in the pathogenicity of the virus, at least with regard to the neurovirulence, has occurred due to the recombination process in the MVA virus, and that there is a large difference in the neurovirulence of the MVA viruses (MVA WT and MVA 5.1) compared with the other vaccinia viruses.

TABLE III

| Neurovirulence in mice |
| --- |
| Log $LD_{50}$ |
| WR WT = −8.7 |
| WR 5.1 = −7.7 |
| LS WT = −5.8 |
| MVA WT = −1.6 |
| MVA 5.1 = −1.5 |

Many modifications and variations of this invention may be made without departing from its spirit and scope, as will become apparent to those skilled in the art. The specific embodiments described herein are offered by way of example only, and the invention is to be limited only by the terms of the appended claims.

I claim:

1. A modified vaccinia virus Ankara useful in vaccine formulations, said virus comprising a DNA sequence which codes for a foreign antigen without impairing the viability of the MVA, which foreign antigen causes infection or disease.

2. The virus of claim 1 wherein said foreign antigen is malaria parasite *Plasmodium falciparum*.

3. A vaccine formulation comprising an effective amount of a modified vaccinia virus Anhara comprising a DNA sequence which codes for a foreign antigen without impairing the viability of the MVA, which foreign antigen causes infection or disease, and a physiologically acceptable carrier.

4. A method for the prophylatic protection of humans or animals against an infection caused by a pathogenic agent exhibiting pathogenic properties, which method comprises the use of the vaccine formulation of claim 3.

5. The vaccine formulation of claim 3 wherein said pathogenic agent is malaria parasite *Plasmodium falciparum*.

* * * * *